United States Patent [19]

Schechter et al.

[11] Patent Number: 5,685,840
[45] Date of Patent: Nov. 11, 1997

[54] METHOD AND APPARATUS FOR MINIMALLY INVASIVE TISSUE REMOVAL

[75] Inventors: Alan M. Schechter, Long Beach, Calif.; Frederick R. Stave, St. Joseph, Mich.; Joseph L. Mark, Indianapolis, Ind.

[73] Assignee: Danek Medical, Inc., Memphis, Tenn.

[21] Appl. No.: 486,350

[22] Filed: Jun. 7, 1995

Related U.S. Application Data

[62] Division of Ser. No. 319,126, Oct. 6, 1994, which is a division of Ser. No. 18,045, Feb. 16, 1993, Pat. No. 5,403,276.

[51] Int. Cl.[6] ............................................. A61B 17/20
[52] U.S. Cl. ................................ 604/22; 606/171
[58] Field of Search ........................ 604/22, 49, 50; 606/167, 169, 170, 171, 177, 178

[56] References Cited

U.S. PATENT DOCUMENTS

| | | |
|---|---|---|
| 3,912,168 | 10/1975 | Mullins et al. . |
| 3,993,054 | 11/1976 | Newman . |
| 4,203,444 | 5/1980 | Bonnell et al. . |
| 4,555,645 | 11/1985 | Atkinson . |
| 4,561,431 | 12/1985 | Atkinson . |
| 4,604,089 | 8/1986 | Santangelo et al. . |
| 4,635,621 | 1/1987 | Atkinson . |
| 4,679,596 | 7/1987 | Olson . |
| 4,911,161 | 3/1990 | Schechter . |
| 5,269,798 | 12/1993 | Winkler ......................... 606/170 |
| 5,275,607 | 1/1994 | Lo et al. ........................ 606/170 |
| 5,286,253 | 2/1994 | Fucci ............................. 604/22 |
| 5,364,395 | 11/1994 | West, Jr. ....................... 604/22 X |
| 5,403,276 | 4/1995 | Schechter et al. ............ 604/22 |

OTHER PUBLICATIONS

Publication: Automated Percutaneous Lumbar Diskectomy, by Gary Onik and Clyde A. Helms; Commentary by H.M. Herkowitz, M.D.; published 1991.

Brochure: The Simple Solution, by Linvatec Concept Arthroscopy; published 1992.

Brochure: Nucleotome System Automated Percutaneous Lumbar Discectomy, by Surgical Dynamics; published 1990.

Brochure: Amset PLD Percutaneous Lumbar Discectomy, by AMC; published 1992.

Official Gazette: Pressure Infusion Device; U.S. Pat. No. 4,735,613 to Bellin et al.; filed Oct. 23, 2986, Ser. No. 922,173; Issued Apr. 5, 1988.

*Primary Examiner*—Michael Powell Buiz
*Assistant Examiner*—N. Kent Gring
*Attorney, Agent, or Firm*—Woodard, Emhardt, Naughton, Moriarty & McNett

[57] ABSTRACT

A method and apparatus for minimally invasive tissue removal contemplates a system including a tissue cutting tool having a motor driven cutting blade reciprocating within a percutaneously introducable cannula. In accordance with one method of the invention, the frequency of reciprocation of the cutting blade is tuned to a characteristic frequency of the target tissue to be excised, which frequency is a function of certain properties of the target tissue and the surrounding tissue. Cutting at the characteristic frequency of the target tissue not only enhances the speed and efficiency of the tissue excision, but also minimizes the risk of cutting surrounding tissue. Another aspect of the system includes feedback control of both aspiration and irrigation circuits of the system. With the feedback control, coupled with user settable inputs, the surgeon can control the system to "tease" tissue into the cutting opening to provide more manageable bite sizes of the excised tissue. Controllable valves and pressure transducers allow the operator to set and maintain the aspiration vacuum and irrigation pressure at optimum levels. In other aspects of the invention, other cutting heads, such as a rasp and a tissue morcelator, are disclosed which take advantage of the integrated feedback control system of the invention.

9 Claims, 4 Drawing Sheets

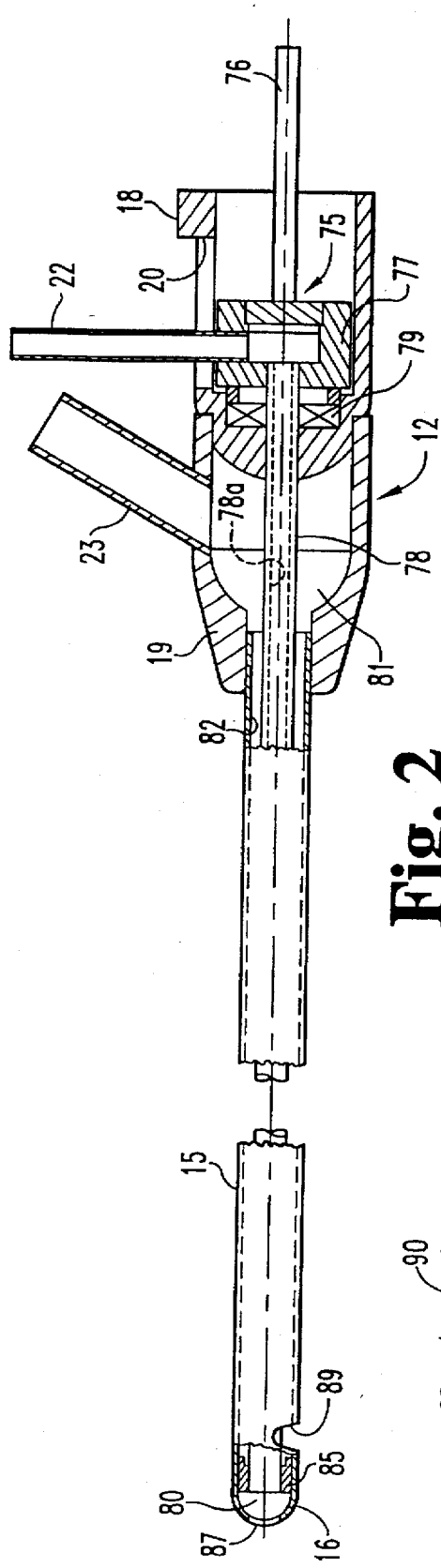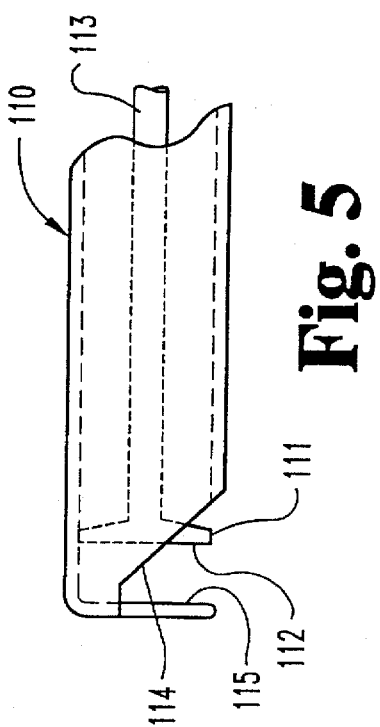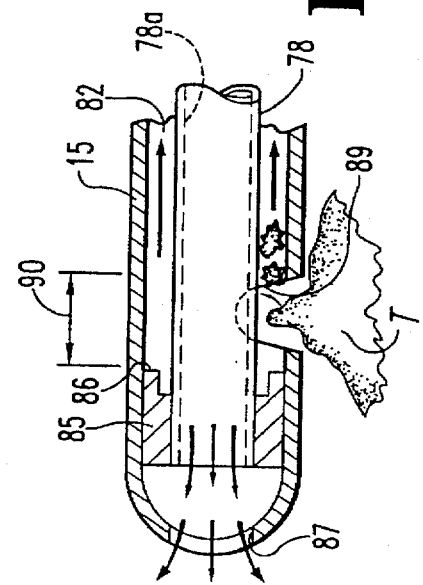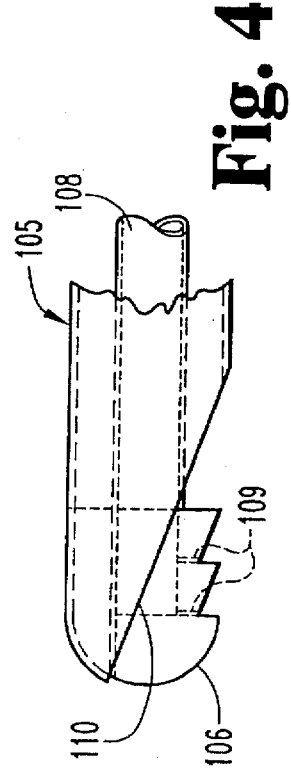
Fig. 2
Fig. 3
Fig. 4
Fig. 5

METHOD AND APPARATUS FOR MINIMALLY INVASIVE TISSUE REMOVAL

This application is a division of application Ser. No. 08/319,126, filed on Oct. 6, 1994 now allowed, which is a division of application Ser. No. 08/018,045, filed on Feb. 16, 1993, which issued as U.S. Pat. No. 5,403,276 on Apr. 4, 1995.

BACKGROUND OF THE INVENTION

The present invention relates to surgical methods and apparatus for the excision and removal of a wide range of tissues. The invention has application for highly delicate procedures involved in areas such as neuro, spinal, orthopaedic, ophthalmic, dental, gynecological, gastrointestinal, urologrical, otolaryngological and cardiovascular, as well as other areas of the body requiring great care in the removal of tissue. While the present invention has application in a wide range of procedures, the following disclosure pertains principally to minimally invasive techniques in the orthopaedic or spinal surgical fields.

In the field of spinal surgery, one problem that is frequently diagnosed and treated concerns degeneration or herniation of the intervertebral disc. Structural changes occur in the disc that may be due to excessive loading conditions or to normal degeneration with age. Intervertebral disc problems can be as simple as the chronic low back pain experienced by a large percentage of the population, or as severe as conditions in which the disc tissue is virtually non-functioning. In the past, treatment of the intervertebral disc has required complicated and highly invasive surgical procedures. Frequently, these procedures require some degree of fusion between adjacent vertebra serviced by the affected intervertebral disc.

Within the last decade, techniques for percutaneous discectomies have been developed. One such system is described in the patent to Onik, U.S. Re. Pat. No. 33,258, and in an article entitled *Automated Percutaneous Lumbar Diskectomy*, dated 1992 in the "Journal of Advances in Orthopaedic Surgery". In the Onik device tissue to be removed is drawn by suction into the central bore of an outer cutting sleeve. A pneumatically driven inner cutting sleeve operates as a guillotine to resect the disc material. The disc material is suspended in a saline irrigation fluid which also assists in aspiration of the resected disc material through the inner cutting sleeve.

While the experiences with this and other similar apparatus for percutaneous discectomy has been favorable, there is naturally room for improvements in the method and apparatus for minimally invasive tissue removal. The procedures using these apparatus are less invasive than prior surgical techniques, but there is still a need to reduce the amount of time required to perform the tissue removal in percutaneous discectomy and similar surgeries. Even the prior art systems are only capable of removing about 0.7 grams of tissue in five minutes. Faster tissue removal translates to quicker procedures and reduced invasion and risk of trauma. In addition, as with any procedure involved in cutting body tissue, there remains a risk with present systems for the tissue cutter to resect desirable tissue as opposed to undesirable tissue sought to be removed. Finally, although all surgical techniques involve some trauma to surrounding tissue, there is a clear need to reduce even further the amount of trauma associated with a percutaneous procedure as contemplated by the present invention.

At present, the state of the art tissue removal systems generally involve the use of motorized pneumatically driven guillotine or rotary type cutters. One problem with these systems is that tissue is often torn, rather than sliced cleanly. With rotary cutters, the tissue has a tendency to become "spooled" or wound around the cutter or drive shaft, thereby clogging or stalling the cutter. These systems also incorporate a gravity fed saline infusion to provide irrigation fluid at the cutting end. The flow of irrigation fluid is controlled manually by varying the height of the fluid source. In the absence or a controllable fluid source, these prior systems require a significant supply of irrigation fluid in order to have enough fluid available for a given procedure. Moreover, these prior systems provide aspiration vacuum by way of a peristaltic or diaphragmatic pump. These prior vacuum systems are often inefficient at drawing tissue into the cutting opening and can be susceptible to clogging as too much tissue is drawn into the cutting port. Inefficiencies in the irrigation and aspiration of the prior art devices often limit the tissue removal capacity so that often the prior devices cannot remove enough tissue to reduce disc herniation, for example, and the associated pain to the patient.

These features of the prior systems lead to inherent limitations in the ability to remove tissue and the speed of the tissue removal. The present invention addresses these and other problems of the prior art devices to greatly advance the field of minimally invasive percutaneous tissue removal.

While the focus of the present description is on spinal or orthopaedic applications, similar tissue removal apparatus and methods can be applied to tissue removal at other sensitive or delicate sites. One example is in the field of neurosurgery, and specifically removal of tumors, blood clots, lesions, aneurysms or membranes. Prior art devices have been generally ineffective in neurosurgery applications. Other examples of broader use of the present invention is in the urological field for removal of the prostate, gynecological surgery for removal of ovaries and lesions, gastrointestinal surgery for removal of the gallbladder and kidney/gall stones, cardiovascular procedures for removal of plaque, and ophthalmology for treatment of cataracts.

DESCRIPTION OF THE DRAWINGS

FIG. 2 is a side partial cross-sectional view of the cutting apparatus shown in FIG. 1 for use in accordance with the present invention.

FIG. 3 is an enlarged partial cross-sectional view of the tip of the cutting apparatus shown in FIG. 2.

FIG. 4 is an enlarged side elevational view of an alternative embodiment of the cutting tip of a cutter for use in the system shown in FIG. 1.

FIG. 5 is a side elevational view of a further alternative embodiment of the cutter for the cutting tool used in connection with the system of FIG. 1.

SUMMARY OF THE INVENTION

Figure 1:
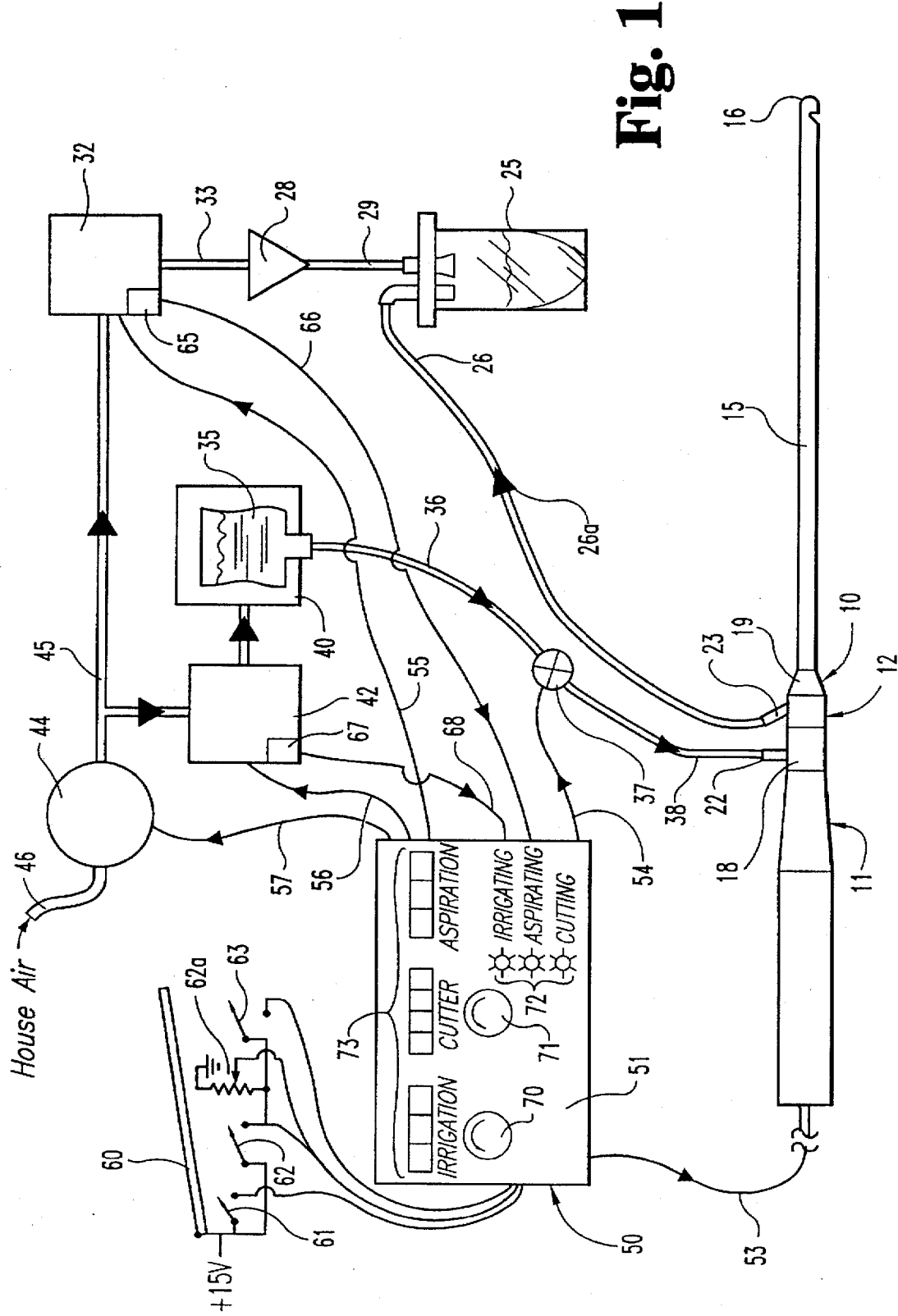
FIG. 1 is a view of a preferred embodiment of the system for minimally invasive tissue removal/n accordance with the present invention.

The present invention contemplates a system for minimally invasive percutaneous tissue removal using a handheld cutting tool. The cutting tool includes a handpiece and an elongated cannula supported on the handpiece which is sized for percutaneous introduction into the body. (Alternatively, the same cutting tool can be used in open surgical procedures). The cannula defines a cutting opening at its distal end and an aspiration channel therethrough from the proximal end to the cutting opening. A cutting blade is slidably mounted within the cannula adjacent the distal end for passage across the cutting opening and is reciprocated across the cutting opening to excise tissue extending into the opening. The excised tissue is removed by an aspiration circuit which includes a waste container and vacuum generator means for generating a vacuum to suck excised tissue into the waste container.

The system further comprises an irrigation circuit which includes a source of irrigation fluid and means for flowing pressurized irrigation fluid from the source to the distal end of the cannula. A master controller is provided for controlling the vacuum generator means and the pressurizing means in accordance with operator preset values for aspiration vacuum level and irrigation pressure. The controller includes circuitry for producing an aspiration control signal and a pressure control signal in response to the preset values. Means responsive to the aspiration control signal are provided for controlling the vacuum generator means to produce and maintain a vacuum equal to the preset aspiration vacuum level value. Similarly, means responsive to the pressure control signal are also provided for controlling the pressurizing means to pressurize and maintain the irrigation fluid at the preset pressure value.

In accordance with the system of the present invention, both the vacuum generator means for the aspiration circuit, and the pressurizing means for the irrigation circuit include controllable valves connected to a source of high pressure gas. Each of the valves controllably reduces the high pressure inlet gas for releasing a relatively reduced pressure gas at their respective outlets. The outlet of the valve in the aspiration circuit is connected to a vacuum generator which produces a vacuum based upon the pressure of the gas it receives from the controllable valve. In the irrigation circuit, the irrigation fluid is contained in a flexible container which is surrounded by a pressure sleeve. The pressure sleeve receives the reduced pressure gas from its corresponding controllable valve so that pressure within the sleeve pressurizes the flexible container and the fluid contained therein.

In one specific embodiment, means are provided for sensing the fluid pressure in the irrigation circuit at the tissue cutting tool and for providing feedback to the controller based upon this sensed fluid pressure. The controller compares the sensed pressure signal with the preset irrigation pressure value to determine whether the fluid pressure in the irrigation circuit must be increased or decreased to meet the preset value.

In another aspect of the invention, the master controller provides means for the surgeon or operator to control the aspiration circuitry to assist in "teasing" tissue into the cutting opening. In particular, the invention contemplates operator control means for variably controlling the vacuum generator means to produce a variable vacuum up to the preset value. In the method of using this system, the operator can selectively draw tissue into the cutting opening by increasing or decreasing the vacuum through the aspiration circuit. It has been found that prior systems in which the vacuum is completely on or completely off, either draw too much or too little tissue into the cutting opening. With this feature of the present invention, the surgeon can interactively control the aspiration rate and suction at the cutting site to draw the optimum amount of tissue into the cutting opening, thereby enhancing the efficiency and speed of the tissue removal procedure.

The present invention further contemplates a novel method for excision of target tissue from the body using a cutting tool having a reciprocating motor driving a cutting blade across a cutting opening in a percutaneously introduced cannula. In this method, the surgeon first determines certain properties of the target tissue and the surrounding tissue that affect how the tissue is cut. Such tissue properties include the elasticity and strength of both target and surrounding tissue. These tissue properties can be correlated to a characteristic frequency of the target tissue and the surrounding tissue. In accordance with the method, the cutting tool speed is controlled so that the cutting blade reciprocates across the cutting opening at the characteristic frequency of the target tissue. It has been found that reciprocating at this tissue specific characteristic frequency increases the speed of the tissue removal. Perhaps most significantly, this tuned tissue cutting substantially prevents cutting of the surrounding tissue. The method of this invention can further include controlling aspiration/vacuum to draw tissue into the cutting tool at an optimum rate.

In further feature of the invention, a surgical rasp is provided for use in percutaneous tissue removal. A rasp blade forms part of a motor driven cutting tool of the type described above. The drive shaft providing reciprocating motion to the rasp blade defines an irrigation channel therethrough. The rasp blade includes a plurality of teeth and defines several apertures between the teeth which communicate with the irrigation channel. These apertures allow pressurized irrigation fluid to pass therethrough to expel excised tissue from between the teeth. In one specific embodiment, the outer cannula of the surgical rasp includes a rounded tip with the cutting opening extending into the rounded tip so that a portion or the rasp blade is exposed beyond the distal end of the cannula.

A tissue morcellator is also provided by the invention for use in percutaneous or open tissue removal. Again, a similar handpiece and drive motor arrangement is contemplated for the tissue morcellator. With this feature, the cannula includes tissue introduction opening at its distal end and an end surface at the distal end facing the introduction opening. A tissue impactor engaged to the reciprocating motor drive shaft includes an impacting surface arranged to oppose the end surface of the cannula. Tissue drawn into the introduction opening is disposed between the end surface and the impacting surface as the impactor is reciprocated by the motor.

DESCRIPTION OF THE PREFERRED EMBODIMENTS

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

According to a preferred embodiment of a tissue removal system in accordance with the invention, as depicted in FIG. 1, a tissue cutting tool 10 is provided which includes a disposable cutter component 12 connected to a handpiece 11. The disposable cutter 12 includes an outer cannula 15 and a cutting end 16 which is adapted to be introduced at the site of the tissue removal. The cutter 12 has a connector base 18 for engaging the handpiece 11, and an integral cannula support body 19 for engaging the cannula 15. The connector base 18 includes an irrigation port 22 extending therefrom, while the cannula support 19 includes an aspiration port 23. The two ports are used to provide irrigation fluid and aspiration vacuum at the cutting end 16 of the disposable cutter 12, as will be described in more detail herein. Alternatively, irrigation can be provided through a separate introducer cannula disposed about the cannula 15 and defining an external irrigation channel.

The system further includes a waste reservoir 25 which receives excised tissue from the cutter by way of an aspiration inlet line 26. The inlet line 26 is connected to the aspiration port 23 of the disposable cutter 12. A vacuum generator 28 is connected to the waste reservoir 25 by way of a vacuum line 29, to provide a vacuum in the reservoir 25 and apply aspiration suction along the aspiration inlet line 26 in the direction of the arrow 26a. The vacuum generator 28 is linked to a controllable valve 32 by way of a pressure line 33. The controllable valve 32 in combination with the vacuum generator 28 provide a means within the present invention for continuously adjusting and linearly controlling the level amount of vacuum actually applied to the waste reservoir 25 and ultimately at the cutting end 16 of the disposable cutter 12. In a specific embodiment, the vacuum level can be varied from zero (0) to 25 in. Hg. Prior art devices simply utilize an on-off type vacuum generator so that when the generator is on, suction is applied to the cutter, and when it is off, no further aspiration is possible. Moreover, prior devices utilize peristaltic or diaphragm pumps which provide inherent delays before the full set vacuum level is achieved and which are often inefficient at yielding high vacuum levels at the cutting site. The present invention provides nearly immediate vacuum at the operator preset level when activated, due to the presence of the controllable valve. One such valve is sold by Proportionaire, Inc. as model no. BB1.

The system further includes an irrigation fluid bag 35 which is connected by way of a fluid outlet line 36 to a pinch valve 37. The outlet of the pinch valve 37 is connected to the irrigation port 22 of the disposable cutter 12 by way of a fluid inlet line 38. The irrigation fluid bag 35 would typically contain a balanced sterile saline solution (BSS), which is fed into the disposable cutter 12 to pass to the cutting end 16 of the cutter. The pinch valve 37 can be controlled to vary the amount of flow of fluid from the fluid bag into the irrigation port 22 of the cutter 12. This irrigation system can work equally well when the BSS is replaced by an insufflation gas when necessary to inflate and maintain the working site.

The irrigation fluid bag 35 is surrounded by a pressure sleeve 40. The sleeve 40 is connected to a controllable valve 42 which provides pressure to the sleeve 40 around the fluid bag 35. Increasing pressure from the controllable valve 42 into the sleeve 40 increases the amount of pressure applied to the fluid bag 35, and consequently increases the pressure and flow rate of irrigation fluid into the disposable cutter 12. A system similar to the pressure infusion device shown in U.S. Pat. No. 4,735,613, may be implemented in connection with a controllable pressure valve, such as the valve 42. Preferably, the valve 42 operates to maintain the pressure value preset by the operator.

Both of the controllable valves 32 and 42 are supplied with pressurized air, or a compressed inert gas, by way of a pressure outlet line 45 extending from a pressure regulator 44. House air can be provided to the pressure regulator 44 by way of a inlet line 46. While house air available at a typical surgical site is supplied at 70–120 psi, according to one specific embodiment of the invention, the pressure regulator 44 maintains the pressure provided through the outlet line 45 and is applied to both valves 32 and 42 at about 70 psi.

The system further includes an electrical controller 50 which receives and provides signals to the various components to control or monitor their operation. The controller 50 includes a console 51 with a variety of switches and displays. The controller 50 provides control signals to the handpiece 11 via a motor drive control line 53. The handpiece 11 of the preferred embodiment is substantially similar to the apparatus shown in U.S. Pat. No. 4,911,161, issued to one of the co-inventors of the present application. Rather than operating pneumatically as prior devices, this handpiece uses a magnetically driven transducer, or voice coil, to provide reciprocating motion to the cutting implement of the disposable cutter 12. The construction and application of the handpiece and motor is partially described at column 5, lines 4–6 and column 6, line 2, which description is incorporated herein by reference. For the purposes of the present disclosure it can be pointed out that the signal on drive control line 53 provides a variable voltage and current to the voice coil motor to control both the amplitude and speed of its oscillation.

The controller 50 further includes a pinch valve control through line 54 which determines when and how much the valve 37 will operate to restrict fluid flow to inlet line 38 into the cutting tool 10. An aspiration valve control line 55 extends from the controller 50 to the controllable valve 32 which provides pressure to the vacuum generator 28. Signals to the controllable valve 32 through line 55 are used to control the amount of vacuum applied to the waste reservoir 25 and the remainder of the aspiration system. A pressure regulator control line 57 integrates the pressure regulator 44 into the control system of the electrical controller 50. This feature allows a pressure value to be preset and automatically maintained.

An irrigation valve control line 56 extends from the controller 50 to the second controllable valve 42. Signals transmitted via line 56 control the amount of pressure applied to the irrigation fluid bag 35 by way of the pressure sleeve 40, which in turn controls the pressure and flow of irrigation fluid into the cutter at the site of the tissue removal.

The controller 50 also receives electrical signals from the various components of the system. For instance, a pressure transducer 65 associated with the aspiration controllable valve 32, sends a signal along line 66 to the controller. Similarly, a pressure transducer 67 associated with the irrigation controllable valve 42, sends a signal along line 68 to the controller. Both of these signals are representative of the pressure provided through the two valves to their respective components (the waste reservoir 25 and the pressure sleeve 40, respectively). Thus, the transducers provide immediate feedback to the controller, which in turn can provide signals to the pressure regulator 44, aspiration controllable valve 32, irrigation controllable valve 42, and pinch valve 37. For example, if the irrigation pressure transducer 67 senses a pressure below an expected value, a feedback signal on Line 68 directs the controller 50 to send an adjustment signal back to controllable valve 42 on line 56. Similar feedback applies to controllable valve 32. In this specific embodiment, pressure transducer 65 indirectly senses the applied vacuum, since vacuum generator 28 creates a vacuum indirectly proportionate to the air pressure fed to it by controllable valve 32

The user can preset the operating parameters of the system by input to the controller, by way of a foot pedal 60 and knobs on the console 51. The foot pedal 60 can be depressed to activate a number of switches in sequence. The first switch in the sequence is the irrigation control switch 61, the second is the aspiration control switch 62, and the final switch is a cutter control switch 63. As the foot pedal is depressed, it contacts and closes the circuit for irrigation control switch 61 first. Further depressing the foot pedal 60 causes the closure of suction/aspiration control switch 62, which causes the vacuum to build instantly and rise at a linear rate. Finally, when the foot pedal is completely depressed the last switch 63 for the cutter control is depressed. In this manner, the sequence of activities at the disposable cutter 12 is predetermined. Irrigation fluid is provided first, followed by aspiration/suction at the cutting site. Once the two precursor operations have been established, the cutting procedure can begin when the pedal is depressed further. Aspiration continues to be variably controlled by the foot pedal.

Further control of the system is achieved by way of control knobs 70 and 71 on the console 51. One control knob 70 controls the irrigation pressure while the second knob 71 controls the speed of the cutting tool 10, by controlling the speed/frequency of the driving motor. It is contemplated that the two knobs 70 and 71 each manipulate a respective rheostat which changes the voltage applied to the lines 56 and 53. Alternatively, the controller 50 can be an electronic controller, in which case the knobs 70 and 71 can provide a signal to the controller to establish a set pressure for the irrigation fluid and speed of operation for the cutter. The signals for the transducers 65 and 67 can be compared to set points established by the knobs 70 and 71. Additional circuitry or software within the electric controller 50 then provides appropriate signals to the controllable valves 32 and 42, and pinch valve 37 to adjust their operation and to maintain the operator preset value. In one specific embodiment, the signal on line 54 to pinch valve 37 is an on/off signal produced by an operator controlled foot pedal.

The console 51 includes operation lights 72, one for each function of the disposable cutter. As the foot pedal 60 is depressed, each of the corresponding lights for irrigation, aspiration and cutting are illuminated. The console 51 further includes an analog display 73 to show the appropriate set pressures and speeds. For instance, the display 73 includes a display for the positive pressure being applied to the irrigation fluid, one for the speed of the cutter operation, and a third display to show the amount of vacuum applied through the aspiration circuit of the system. The irrigation pressure and aspiration vacuum displays receive signals from the respective transducers 67 and 65, while the cutter speed display in one specific embodiment is connected directly to the control knob 71. Alternately, a speed sensor can be mounted in the handpiece to directly determine the motor and cutter speed.

The details of the disposable cutter 12 are shown with reference to FIG. 2. As previously mentioned, the disposable cutter 12 is adapted to engage a handpiece 11 in accordance with the cutting apparatus described in U.S. Pat. No. 4,911,161. In order to integrate the disposable cutter 12 with the handpiece 11, a drive interface 75 is provided that includes a connector chuck 76, similar to the toggle described in the '161 patent at column 6, lines 32–38, which description is incorporated herein by reference. The connector chuck 76 is affixed to a port connector body 77 together with the irrigation port 22. The port 22 extends through a slot 20 in the connector base 18 of the disposable cutter 12. It should be understood that the connector chuck 76 is engaged to the voice coil motor of the handpiece 11 which produces oscillating linear motion. Since the irrigation port 22 is connected to the oscillating connector chuck 76 it also moves back and forth within the connector base 18. The slot 20 accommodates this reciprocating motion of the port 22. Alternatively, port 22 can feed fluid to a separate closed chamber within base 18, with the driving component supported by seals at the ends of the chamber. In this alternative embodiment, the slot 20 can be eliminated since the port 22 would remain fixed to the base 18.

The drive interface further includes a drive tube 78 which is connected with the port connector body 77 so that it too oscillates as the voice coil motor operates. (Note that when irrigation fluid is supplied through an external cannula, tube 78 can be replaced by a solid drive rod). The drive tube extends distally through the cannula 15 and is closed at one end by a seal 79 mounted within the cannula support body 19. The drive tube 78 extends through the entire length of the outer cannula 15 with its free end 80 disposed at the cutting end 16 of the cutter 12. The internal passageway 78a of the drive tube 78 then opens at this end 80 so that irrigation fluid is directed from the irrigation port 22 all the way to the cutting end of the apparatus. The irrigation outflow end 80 of the drive tube 78 is supported by the cutter 85 itself, which cutter slides within the outer cannula 15 at the cutting end 16.

The disposable cutter 12 further includes the cannula support body 19 into which the outer cannula 15 is engaged. The cannula support body 19 is affixed to the connector base 18 as part of the disposable cutter assembly 12. The cannula support body 19 defines an aspiration cavity 81 which communicates with the aspiration channel 82 extending along the entire length of the outer cannula 15. The channel 82, cavity 81 and aspiration port 23 form part of the vacuum circuit which applies aspiration suction or vacuum at the cutting end 16 of the tool 10.

An irrigation orifice 87 is formed in the tip of the outer cannula 15 to infuse the cutting site with irrigation fluid that has passed through port 22, port connector body 77, and drive tube 78. The disposable cutter 12 further includes a cutting blade 85 affixed to the end of the drive tube 78. The cutting blade 85 has an outer diameter nearly equal to the inner diameter of the aspiration channel 82 to thereby provide some sealing effect at the end of the drive tube 78 so that the aspiration vacuum applied at the cutting opening 89 in the side of the cannula 15 is as close as possible to the expected vacuum level. The cutting blade 83 includes a rearwardly facing cutting edge 86 (that is, facing toward the handpiece), which slices the tissue with each reciprocation of the blade 85. As shown in the more detailed view of FIG. 3, the cutter 85 in the preferred embodiment has a cutter travel distance 90 which is slightly greater than the width of the cutting opening 89 to provide for complete excision of the tissue to be removed. Alternatively, the cutter can be configured to cut on the forward stroke, if, for example, aspiration is accomplished through drive tube 78.

Referring again to FIG. 3, the operation of the disposable cutter 12 can be explained. As previously discussed, irrigation fluid passes through drive tube 78 and exits the end of the outer cannula 15 through orifice 87. When the foot pedal 60 (FIG. 1) is depressed, the irrigation control switch 61 is engaged first so that the first step of operation is the introduction of irrigation fluid to the cutting site. In one important aspect of the invention, the electronic controller 50 allows the operator to vary the irrigation pressure by way of control knob 70. The controller 50 receives signals from the pressure transducer 67 along line 68 from the controllable valve 42 and then adjusts the amount of air pressure passing through the controllable valve to the pressure sleeve 40 based on the feedback from the transducer. In this manner, the pressure applied to the irrigation fluid bag 35, and consequently the pressure and flow rate of the irrigation fluid passing through channel 82, is regulated and maintained at the set pressure. The operator can change this irrigation fluid flow by adjusting the control knob 70 as required for a particular application. Too much irrigation fluid pressure/flow can cause turbulence at the cutting site so that the tissue T does not fully enter the cutting opening 89. Too little irrigation fluid can lead to a similar result. Prior art devices With no control of irrigation pressure can also cause tissue damage due to turbulence and swirling. Since the prior art devices have no variable control, a large reservoir of irrigation fluid must be maintained to provide sufficient fluid throughout the entire procedure.

As the pedal 66 is further depressed, the aspiration control switch 62 is depressed which causes the vacuum generator 28 to produce an aspiration vacuum in the aspiration channel 82. This vacuum has a tendency to draw both irrigation fluid and the subject tissue T into the cutting opening 89. While the irrigation pressure may generally be expected to remain constant at the pressure level set by control knob 70, the aspiration or vacuum level is anticipated to be varied in accordance with the present invention. Specifically, as previously described the aspiration system is initiated when the foot pedal 60 closes the switch 62. The aspiration or suction control switch 62 also includes a variable resistance switch component 62a which applies a variable voltage to the aspiration controllable valve 32 based upon the amount the foot pedal 60 is depressed. In this manner, the operating physician by simply varying the amount of pressure on the foot pedal 60 can control the amount of aspiration suction applied through the aspiration channel 82.

One specific benefit obtained by this feature of the invention is the ability to "tease" tissue into the cutting opening 89. In prior systems, the vacuum is either on or off, and is typically set at a fixed vacuum level. Thus, these prior systems are prone to generating excessive fluid flow and turbulence at the cutting opening which not only decreases the efficiency of the cutting process but also adds to the possible damage to surrounding tissue. Many of the prior devices are inefficient due to their tendency to push tissue away from the cutter, which then forces the surgeon to "chase" tissue to be excised. The present invention alleviates this problem by enhancing the "followability" of the tissue into the cutting opening 89. In experiments with embodiments of this invention, it has been found that tissue being cut by the present device invaginates onto itself in the region of the cutting opening, thereby continuously drawing tissue into the opening.

With the controller 50, controllable valves 32 and 42, and the variable switch 62, an effective balance can be maintained between the irrigation fluid injected to the cutting site and the vacuum applied to draw the tissue into the cutting opening and to aspirate the cut pieces of tissue. With the foot pedal 60 and variable switch 62a, the operator can continually change the vacuum-level as required to draw well proportioned pieces of tissue T into the cutting opening as the cutter blade 85 reciprocates within the aspiration channel 82 of the outer cannula 15. The display 73 gives the operator an opportunity to tune and preset both the irrigation pressure and the aspiration vacuum and maintain those values at optimum levels during the procedure.

Once irrigation and aspiration/suction is established, further depressing the foot pedal 60 closes the cutter control switch 63 which energizes the voice coil motor in the cutter 10. (It is contemplated that a separate pedal could be provided for controlling the motor and cutter speed). The cutter control switch 63 is depressed and operative while the operator is varying the pressure on the variable switch 62a for the irrigation control. The control knob 71 varies the frequency of the voice coil motor to thereby control the speed of the reciprocating cutting blade 83. A suitable control circuit for the voice coil motor can be as shown in FIG. 3 of the '161 patent and as described in the accompanying portion of the specification at column 5, lines 54–59, which description is incorporated herein by reference. In essence, the voice coil oscillates the cutting blade 85 so that the cutting blade passes back and forth across the cutting opening 89. In one specific embodiment, the voice coil motor can drive the cutting blade 85 at between 1 (one) and 500 hertz. The amplitude of the voice coil oscillation translates directly to the cutter travel or stroke 90. Preferably the stroke is slightly wider than the maximum width of the cutting opening 89 so that the blade is clear of the opening toward the distal end to allow tissue to be drawn into the opening by vacuum through the aspiration channel 82, and travels far enough across the opening toward the proximal (handpiece) end to cleanly shear the tissue off at the edge of the cutting opening 89.

One important feature of the method of the present invention is accomplished by tile variable speed of the cutting blade 85 as controlled by the cutter speed control knob 71 and controller 50. It has been discovered that body tissue exhibits selective cutting properties so that they can be optionally cut at a certain frequency. This frequency will vary based upon the type of tissue being cut—that is membranes, skin, muscle, veins or arteries, organs, etc. One of the goals of the present invention, which until now were not met by prior devices, is to produce a smooth, clean, tear-free cutting of the tissue T. In addition, another goal which is also lost on several prior art devices is the ability to cut only the tissue that needs to be excised without any risk of accidentally cutting adjacent desirable tissue. It was discovered that the selective cutting properties of various tissues is an important feature to exploit to achieve each of these goals. It is believed that the selective cutting properties of the tissue are based upon the elasticity, fibrotic content and hardness/softness of the tissue. All of these characteristics yield a specific "resonant" frequency at which the tissue is optimally cut in either a shaving or a slicing action. These tissue specific cutting frequencies can be derived empirically for various tissues by testing with a variety of cutting blades. It has been further discovered that this frequency can be affected to some degree by the geometry of the blade 85 and cutting opening 89. The geometry of the cutting opening 89 determines the "bite size" of the tissue being drawn into the opening. For tougher fibrous tissue a greater cutting area is required so that the cutting opening 89 can be somewhat larger than for less fibrous tissue.

The "resonant" frequency characteristics of body tissue can be readily exploited by the present invention which contemplates real time variation in the speed of the cutter blade 85. When spinal disc tissue is being cut, for instance, the control knob 71 can be set so that the cutter oscillates at the appropriate speed for that type of tissue. In this manner the risk of damage to surrounding tissue is greatly minimized. A proper combination of stroke length 90 and size of the cutting opening 89 further enhances the ability for the disposable cutter 12 to effect a smooth, clean, tear-free, straight line cut of bite size pieces of the tissue.

Figure 7:
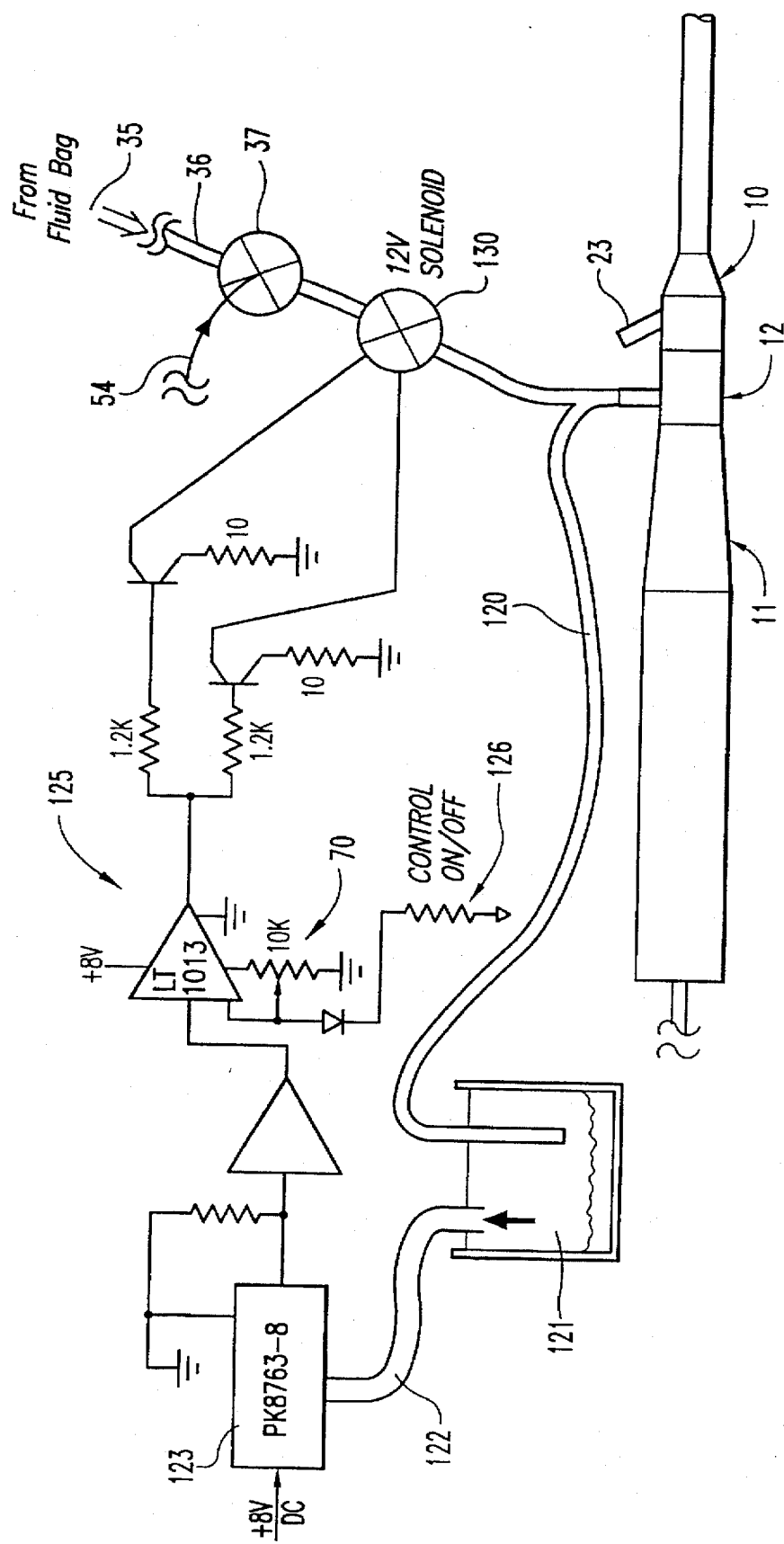
FIG. 7 is a schematic of an alternative embodiment of the fluid system for use with the system shown in FIG. 1, this alternative embodiment providing pressure feedback control for the irrigation fluid provided to the cutter.

As has previously been discussed, the integration between the irrigation pressure and the aspiration vacuum is achieved by the switch 70 and variable switch 62A. Further control can be provided by way of the pinch valve 37 which is foot switch actuate as previously described. The operator can open of close the pinch valve to start or stop the vacuum as needed to tease tissue T into the cutting opening 89. An optimum amount of fluid pressure is important at the cutting site to help tease the tissue T. Further benefits can be attained by a pressure feedback system as depicted in FIG. 7. In this system, a pressure sensing line 120 taps into the fluid outlet line 36 connected to the fluid bag 35. Fluid pressure is transmitted along sensing line 120 to a pressure buffer 121, which serves to insulate the downstream components from the fluid. A sensor inlet 122 provides a pressure signal to a pressure transducer 123, which optimally is mounted within the console 51. The transducer 123 yields an electrical signal that is fed to conditioning electronics 125. Further inputs to the electronics 125 are provided by the irrigation control knob 70 which determines the operator preset irrigation pressure value, and by an on/off swatch 126. The electronics 125 integrates these three electrical signals to produce a control signal to a solenoid pinch valve 130.

In operation, the pressure transducer 123 produces a signal indicative of the fluid pressure being provided to the handpiece 10. As this pressure signal varies from the preset value established by control knob 70, the electronics 125 varies the state of the solenoid pinch valve 130 to allow more or less fluid to the handpiece. Optimally, the fluid pressure upstream of the pinch valve 130 is higher than the user preset value. This higher pressure can then be accurately reduced by the pinch valve 130 if the pressure at the handpiece is higher than the expected preset value. While a fluid pressure line 120 is disclosed in this specific embodiment, a separate sensor at the cutting tip is contemplated that feeds a signal directly to either the transducer 123 or to the electronics 125.

While one primary application of the fluidics and control system of the present invention is for the cutting blade 85, other types of cutting heads are contemplated. For instance, as shown in FIG. 4, a rasp type cutter 106 is shown reciprocating within an outer cannula 105. The rasp cutter 106 includes serrated teeth 107 which are uniquely adapted to prepare the end plates of a spinal disc. In a number of disc procedures, it is necessary to reduce the vertebral end plate to "bleeding bone" to facilitate fusion between adjacent vertebrae. The rasp cutter 106 is integral with or fixed to an irrigation tube 108 which is also connected to the drive mechanism. Outlet ports 109 are formed between the teeth 107 in communication with the tube 108, fluid passing through the ports 109 not only irrigates the cutting site, but also helps clean the rasp teeth 107 of tissue removed with each cycle. The outer cannula 105 is configured to include an end bevel 110 to allow the rasp teeth 107 to be fully exposed as the cutter 106 oscillates between the ends of the bevel 110.

A further cutting tool is shown in FIG. 5 which includes a tissue morcelator 111 that oscillates within an outer cannula 110. The morcelator 111 includes an impacting face 112. The morcelator is integral with or fixed to an irrigation tube 113 which has an opening at the impacting face 112. The outer cannula 110 includes a tissue opening which is large enough to draw a significant amount of tissue into the outer cannula 110. The cannula also includes an integral opposing impacting face 115 so that the tissue is morcelated between the morcelator 111 and the impacting surface 115. Vacuum applied in the outer cannula helps retain the tissue within the tissue opening 114. This tissue morcelator can be used on both soft and hard tissue.

Figure 6:
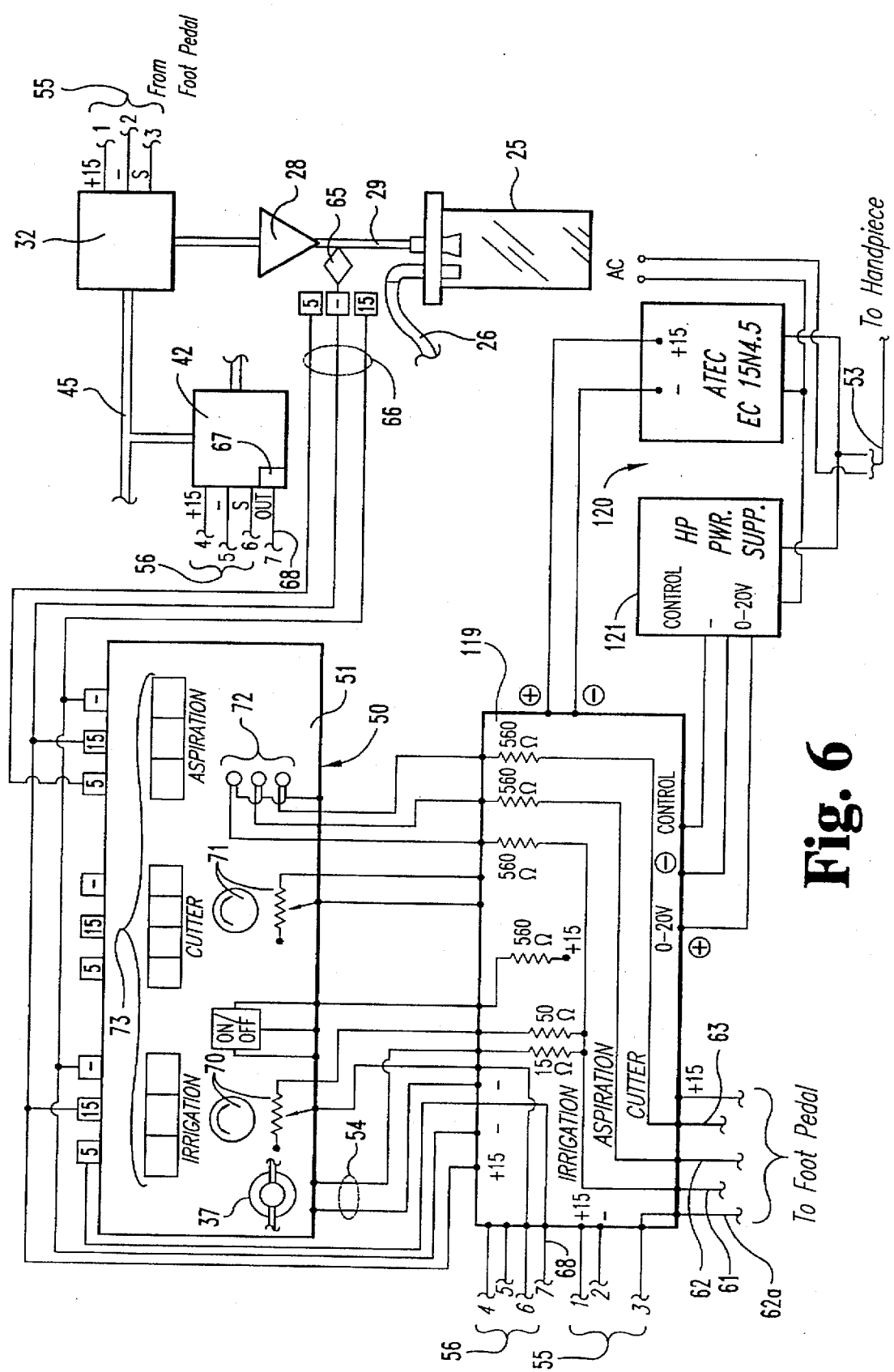
FIG. 6 is a circuit diagram for one embodiment of the system shown in FIG. 1.

Referring now to FIG. 6, the circuit diagram for one specific embodiment of the invention is shown. In this Figure, like figure numbers refer to like components illustrated in FIG. 1. A circuit board 119 includes a number of resistors and wiring paths to integrate the various switches, controllable components, and sensor inputs. The control knobs 70 and 71 are shown with their variable resistance or rheostat components which are used to modulate the voltage provided to the respective controllable valves 32 and 42. The irrigation control knob 70 is not energized until the foot pedal 60 is depressed far enough to close switch 61 thereby sending a signal through to the variable resistant component of switch 70. Similarly, cutter speed control knob 71 is not energized until switch 63 is actuated by depressing the foot pedal 60.

The aspiration/vacuum control set up is somewhat more involved since it includes two switches. The first switch 62 when activated by depressing the foot pedal 60 simply initiates the signal line to the controllable valve 32. The variable switch 62A provides a signal to the controllable valve 32 along valve control line 55 to allow the operator to directly modulate the amount of vacuum produced by the vacuum generator 28.

The electronics of the system allows for reception of sensor signals from both the aspiration pressure transducer 65 and the irrigation pressure transducer 67. In this figure, the aspiration pressure transducer 65 is depicted as tapping into the vacuum line 29 between the vacuum generator 28 and die waste reservoir 25. Locating the transducer signal output along line 66 which directly correlates to the amount of vacuum applied to the aspiration circuitry of the system. The sensor signal passing along line 66 from the pressure transducer 65 to the control components provides immediate feedback to the controllable power supply 121 to maintain the vacuum at the level set by variable switch 62A. Similarly, a sensor signal along line 68 from the irrigation pressure transducer 67 provides feedback to the programmable power supply 121 to maintain the irrigation pressure and flow rate at the value set by control knob 70. The pinch valve 37 is similarly controlled by a signal along line 54, as previously described.

In accordance with the specific embodiment of the present invention, the power supply 120 includes a variable or programmable power supply 121 which can change the voltage provided to the circuit board 119 and other components of the system. The power supply 120 also provides power directly to the handpiece 53 to drive the voice coil motor in the handpiece.

While the invention has been illustrated and described in detail in the drawings and foregoing description, the same is to be considered as illustrative and not restrictive in character, it being understood that only the preferred embodiments have been shown and described and that all changes and modifications that come within the spirit of the invention are desired to be protected.

What is claimed is:

1. A tissue morcellator for use in percutaneous tissue removal, comprising:

a handpiece;

a motor supported by said handpiece having means for producing linearly reciprocating motion;

an elongated cannula sized for introduction into the body, said cannula having a proximal end and a distal end, said cannula supported by said handpiece at said proximal end and having a tissue introduction opening at said distal end and further having an end surface at said distal end facing said introduction opening;

a tubular drive shaft connected to said motor and extending through said cannula to said introduction opening; and a tissue impactor engaged to said drive shaft and having an impacting surface arranged to oppose said end surface of said cannula, whereby tissue extending into said introduction opening is disposed between said end surface and said impacting surface as said impactor is reciprocated by said motor.

2. The tissue morcellator of claim 1, further comprising an aspiration circuit including:

a vacuum source;

an aspiration conduit defined in said cannula or said drive shaft, said conduit fluidly coupled to said vacuum source and having an inlet opening at said tissue introduction opening, whereby vacuum applied by said source through said aspiration conduit draws tissue through said introduction opening in said cannula and between said end face and said impacting surface.

3. The tissue morcellator of claim 2, wherein said drive shaft defines said aspiration conduit and said impactor is integral with said drive shaft.

4. The tissue morcellator of claim 1, wherein said impactor is configured to move back and forth across said introduction opening as said impactor is reciprocated by said motor.

5. The tissue morcellator of claim 1, wherein said impactor has a substantially flat impacting surface.

6. A tissue morcellator, comprising:

a handpiece;

a motor;

an elongated cannula sized for introduction into a patient's body, said cannula having a proximal end and a distal end, said cannula being supported by said handpiece at said proximal end and defining a tissue introduction opening proximate to said distal end;

a drive shaft connected to said motor and extending through said cannula to said introduction opening, said drive shaft being configured to reciprocate within said cannula in response to activation of said motor; and a tissue impactor coupled to said drive shaft to reciprocate across the introduction opening as said drive shaft reciprocates, said impactor being positioned to oppose a surface of said cannula to morcellate tissue located between said surface and said impactor as said impactor reciprocates.

7. The morcellator of claim 6, further comprising an aspiration circuit with a vacuum source and an aspiration conduit defined in said drive shaft, said conduit being in fluid communication with said vacuum source and having an inlet opening at said introduction opening to draw tissue between said impactor and said surface for morcellation.

8. The morcellator of claim 6, wherein said introduction opening is defined along a side of said cannula.

9. The morcellator of claim 6, wherein said impactor has a substantially flat impacting surface.

* * * * *